United States Patent [19]

Abraham et al.

[11] 3,944,541

[45] Mar. 16, 1976

[54] 22-CYANO-24-NORCHOLANES

[75] Inventors: Nedumparambil A. Abraham, Dollard des Ormeaux; Yvon Lefebvre, Pierrefonds, both of Canada

[73] Assignee: American Home Products Corporation, New York, N.Y.

[22] Filed: May 13, 1974

[21] Appl. No.: 469,269

[52] U.S. Cl...... 260/210.5; 424/182; 260/239.55 R; 260/239.57
[51] Int. Cl.² .......................................... C07J 19/00
[58] Field of Search .............................. 260/210.5

[56] References Cited
UNITED STATES PATENTS
3,852,265  12/1974  Hartenstein et al. ............ 260/210.5

Primary Examiner—Johnnie R. Brown
Assistant Examiner—Cary B. Owens
Attorney, Agent, or Firm—John P. Floyd

[57] ABSTRACT

There are disclosed herein the 3β, 14-dihydroxy-, 3β,5,14-trihydroxy-, 3β,12β,14-trihydroxy- and 3β,14,16β-trihydroxy-21,23-epoxy-23-methoxy-24-nor-5β,14β-chola-20,22-diene-22-carbonitriles, as well as their corresponding 3-acetates, 3-propionates and 3-butyrates and their 3-digitosides and 3β-cyamarosyl-glucosides as encountered in naturally-occuring starting materials. The compounds possess useful cardiotonic activity. Also included are the corresponding 22-cyano-5β-card-20(22)-enolides, useful as intermediates in the preparation of the compounds of this invention and also as cardiotonic agents.

3 Claims, No Drawings

22-CYANO-24-NORCHOLANES

BACKGROUND OF THE INVENTION a. Field of the Invention

This invention relates to 21,23-epoxy-23-methoxy-24-nor-5β,14β-chola-20,22-diene-22-carbonitriles, to 22-cyano-5β-card-20(22)-enolide intermediates and to methods of preparing and using these compounds. the compounds of this invention as well as the 22-cyanocardenolide intermediates show cardiotonic activity in mammals and this property renders them useful as cardiotonic agents.

b. Prior Art

The only known 21,23-epoxy-24-nor-5β,14β-chola-20,22-dienes appear to be the 17-[3-furyl]-5β,14β-androstanes described in Canadian Pat. No. 803,506, issued Jan. 17, 1969.

On the other hand, concerning the 22-cyano-5β-card-20(22)-erolide intermediates, some 22-substituted cardenolides are known besides the naturally-occurring glycosides and aglycones (see for example in German Pat. Nos. 1,027,668, 1,920,176, 1,920,394, 2,000,338, 2,001,364 and 2,015,850 and also in Dutch Pat. No. 72-12308 and Belgian Pat. No. 751,768.

SUMMARY OF THE INVENTION

The 21,23-epoxy-23-methoxy-24-nor-5β,14β-chola-20,22-diene-22-carbonitriles of this invention may be represented by the formula I, in which St—OR represents rings

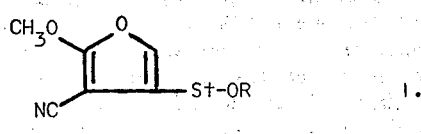

A, B, C and D of 3β-oxygenated aglycones with their respective substituents attached thereto such as digitoxigenin, periplogenin, digoxigenin and gitoxigenin, in which R is hydrogen, a lower aliphatic acyl group containing from 2 to 4 carbon atoms or glycosidic groups naturally associated with the above-mentioned aglycones and in which the 2-methoxy-3-cyanofuryl group is attached to the steroid moiety St at position 17β.

Detailed Description of this Invention

The compounds of this invention possess important cardiotonic properties and are useful as cardiotonic agents.

Cardiotonic agents have the ability to increase the force of contraction of the failing heart and are extensively used in the therapy of congestive heart failure, see for example L.F. Fieser and M. Fieser, "Steroids", pages 799 and 800.

The cardiotonic activity of the compounds of this invention may be demonstrated by their ability to restore the normal force of contraction in mammals in which experimental heart failure has been induced. More particularly, the cardiotonic activity of the compounds may be determined in the following animal model: Mongrel dogs of both sexes weighing from 6 to 15 kg are anesthetized for surgery by the intravenous administration of approximately 35 mg/kg of sodium pentobarbital. The trachea is then cannulated to allow artificial respiration after thoracotomy. The two femoral veins are also cannulated for the infusion of sodium pentobarbital and the intravenous administration of the compounds to be tested. Following thoracotomy and exposure of the right ventricle, a metal-encased strain gauge arch with one movable foot, for example the Walton-Brodie type, is sutured onto the ventricle for the recording of the force of contraction of the heart muscle. The resting tension applied between the two feet of the arch is adjusted to give the maximum tension development during a cardiac contraction. The systolic, diastolic and mean blood pressures are recorded from a femoral artery. The beat to beat heart rate is measured by means of a tachograph, triggered by a signal derived from the amplified pulse pressure wave. Finally the electrocardiogram is simultaneously recorded on a polygraph. Following surgery the above-mentioned parameters are recorded until they remain constant.

Cardiotonic activity may be demonstrated in the following experiment. Experimental heart failure is induced in the above described dogs by the intravenous administration of sodium pentobarbital at a rate of 0.75 mg/kg/min until the force of contraction of the heart as measured by the strain gauge sutured onto the right ventricle is decreased by approximately 50%. In order to maintain the force of contraction at this reduced level sodium pentobarbital is continuously infused at the rate of 0.1 mg/kg/min. Restoration of the force of contraction of the heart muscle to its initial level following the administration of test compounds is a demonstration of cardiotonic activity. The 21,23-epoxy-23-methoxy-24-nor-5β,14β-chola-20,22-diene-22-carbonitriles and the 22-cyano-5β-card-20(22)enolide intermediates of this invention restore the force of contraction of the heart in dogs in which experimental heart failure has been induced as described above. Consequently they exhibit cardiotonic activity in mammals and their property renders them useful as cardiotonic agents.

The dosages of the 21,23-epoxy-23-methoxy-24-nor-5β,14β-chola-20,22-diene-22-carbonitriles and the 22-cyano-5β-card-20(22)-enolide intermediates will depend on the pharmaceutical aim and the particular compound chosen. The compounds are best administered intravenously in sterile solutions or suspensions in pharmaceutically acceptable vehicles in doses ranging from 1 mg to 100 mg/kg. More particularly, in order to restore the force of contraction, the compounds are best given by successive administrations in the form of sterile suspensions and in doses ranging from 10 to 20 mg/kg for the 21,23-epoxy-23-methoxy-24-nor-5β,14β-chola-20,22-diene-22-carbonitriles and in doses of 5 – 10 mg/kg for the 22-cyano-5β-card-20(22)-enolide intermediates, until the desired effect is produced. For maintenance, the compounds are again best administered in the form of sterile suspensions but in reduced dosages, preferably ranging from 1 mg to 5 mg/kg.

Process

The 21,23-epoxy-23-methoxy-24-nor-5β,14β-chola-20,22-diene-22-carbonitriles of this invention are prepared by the process depicted in the following flow sheet.

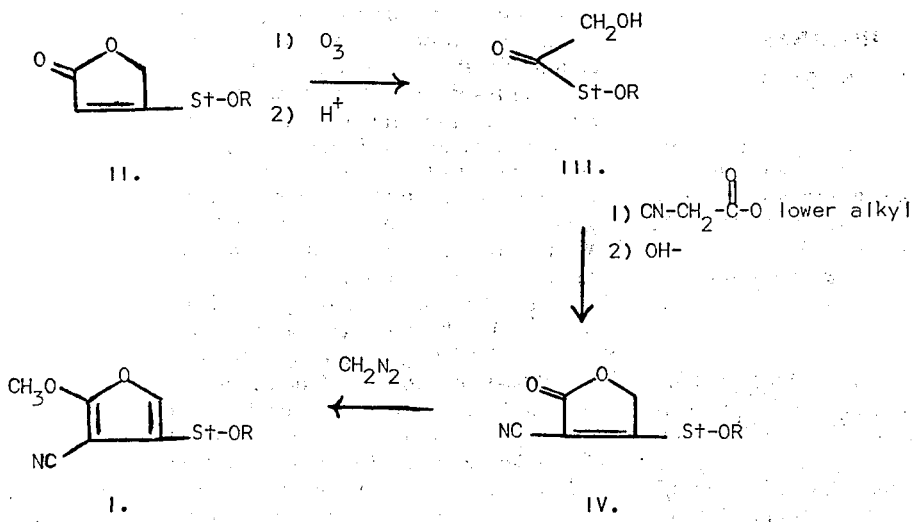

The starting materials of formula II, in which St—OR is as defined above, are naturally-occuring cardiac glycosides such as digitoxin, periplocin, gitoxin and digoxin, their corresponding aglycones, or their 3-lower aliphatic acyloxy derivatives, for example the 3-acetates, 3-propionates and 3-butyrates. The 3-acetates of gitoxigenin and digoxigenin are prepared as described in Elsevier's Encyclopedia of Organic Compounds, Vol. 14S (1969) pp. 4579S and 4561S respectively. Their corresponding 3-propionates and 3-butyrates are prepared according to the same procedures.

The starting materials of formula II are oxonized and then hydrolyzed as described by Bach et al. in Can. J. Chem., Vol. 46, p. 733 (1969) to afford the 21-hydroxy-20-ketones of general formula III, in which St—OR is as described above. The 21-hydroxy-20-ketones of formula III are subsequently condensed with a lower aliphatic ester of cyanoacetic acid, for example methyl or ethyl cyanoacetate, in the presence of a basic catalyst, for example an alkali metal alkoxide, preferably sodium methoxide or potassium t-butoxide, or an alkali metal hydride, preferably sodium hydride, in an inert solvent to afford the 22-cyano-5β-card-20(22)-enolides of formula IV in which St—OR is as described above. 2-Cyano-2-buten-4-olides have been prepared by a similar procedure, see A.A. Avetisyan et al., Zh. Org. Khim, Vol. 7, page 962 (1971), Chem. Abst. Vol. 75, page 63,047q (1971). Finally, the 22-cyano-5β-card-20(22)-enolides IV are converted to the 21,23-epoxy-23-methoxy-24-nor-5β,14β -chola-20,22-diene-22-carbonitriles I of this invention upon reaction with diazomethane.

In a preferred embodiment of this invention, digitoxigenin acetate or digoxin of formula V in which R represents an acetoxy or a tridigitosyloxy group are ozinized according to the procedure described by Bach et al., cited above and hydrolyzed to give the corresponding 14,21dihydroxy-5β,14β-pregnan-20-ones of formula VI. Treatment of the latter compounds with ethyl cyanoacetate in the presence of sodium methoxide in methanol affords the corresponding 22-cyano-14-hydroxy-5β-card-20,(22)-enolides of formula VII, which upon reaction with diazomethane yield the corresponding 21,23-epoxy-14-hydroxy-23-methoxy-24-nor-5β,14β-chola-20,22-diene-22-carbonitriles of formula VIII. Compounds VI, VII and VIII, respectively correspond to compounds III, IV and I in which St—OR represents rings A, B, C and D of digitoxigenin along with the sutstituents attached thereto and R represents an acetoxy or tridigitosyloxy group.

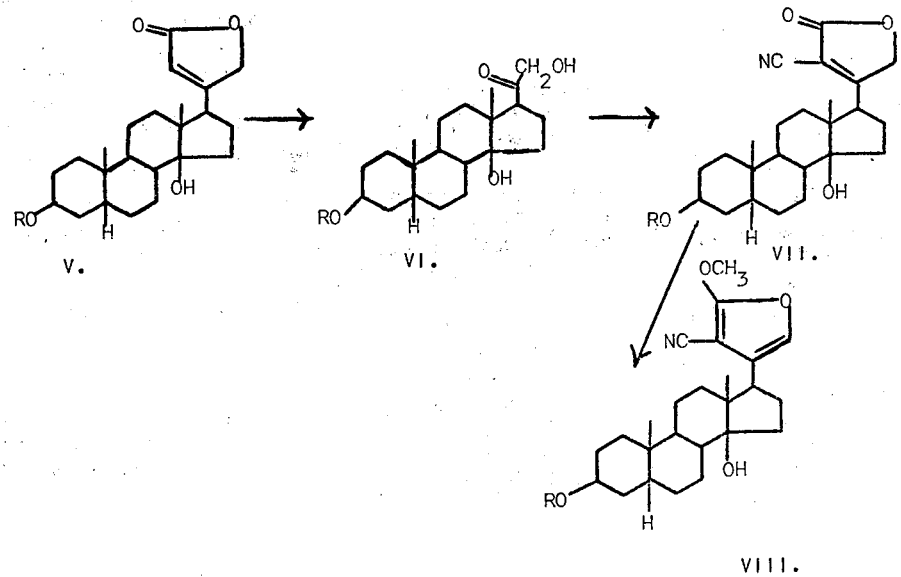

The following examples will serve to illustrate the present invention.

EXAMPLE 1

3β,14,21-Trihydroxy-5β,14β-pregnan-20-one 3-acetate

Ozone is passed through a solution of digitoxigenin acetate (19.8 g) in ethyl acetate (1100 ml) cooled at −70° until a blue color appears. After bubbling nitrogen until the disappearance of the blue color, potassium iodide (11.85 g) and glacial acetic acid (12 ml) are added and the mixture is stirred for 1 hour during which time the temperature is allowed to rise to room temperature. The solution is then washed repeatedly over a period of about 6 hours with a 10% aqueous solution of sodium thiosulfate to remove iodine, dried and evaporated affording crude 3β, 14,21-trihydroxy-5β,14β-pregnan-20-one 3-acetate, 21-glyoxylate.

Without purification a mixture of this product (20.4 g) and a 0.1N solution of hydrochloric acid is left at room temperature for 24 hours. The solution is concentrated to a small volume, while keeping the temperature of the water bath at about 50°C. The residue is extracted with ethyl acetate and ether. The extracts are washed to neutrality, dried and evaporated. The title compound is obtained by crystallization from ether, m.p. 160° – 164°C.

In a similar manner the 3-propionate and 3-butyrate of digitoxigenin are converted to the 3-propionate and 3-butyrate of 3β,14,21-trihydroxy-5β,14β-pregnan-20-one respectively when treated as above.

Similarly, digitoxigenin, periplogenin, digoxigenin and gitoxigenin are converted to 3β,14,21-tri-hydroxy-5β,14β-pregnan-20-one, 3β,5,14,21-tetrahydroxy-5β,14β-pregnan-20-one, 3β,12β,14,21-tetrahydroxy-5β,14β-pregnan-20-one and 3β,14,16β,21-tetrahydroxy-5β,14β-pregnan-20-one respectively when treated as above.

Again similarly the 3-acetates 3-propionates and 3-butyrates of periplogenin, digoxigenin and gitoxigenin are respectively converted to the 3-acetates, 3-propionates and 3-butyrates of 3β,5,14,21-tetrahydroxy-5β,14β-pregnan-20-one, 3β,12β,14,21-tetrahydroxy-5β,14β-pregnan-20-one and 3β,14,16β,21-tetrahydroxy-5β,14β-pregnan-20-one when treated as above.

EXAMPLE 2

3β-Tridigitosyloxy-14,21-dihydroxy-5β,14β-pregnan-20-one

Ozone is passed through a solution of digitoxin (20 g) in methanol (1200) cooled at −70°C until a blue color appears. The solution is allowed to warm up to room temperature and is left standing overnight. After bubbling nitrogen, a solution of potassium iodide (20 g) in water (30 ml) is added followed by glacial acetic acid (0.4 ml). The mixture is then washed repeatedly over a period of approximately 6 hours with a solution of sodium thiosulfate (15 g of $Na_2S_2O_3 5H_2O$) in water (30 ml) to remove free iodine. Finally a solution of potassium bicarbonate (15 g) in water (700 ml) is added and the mixture is stirred overnight at room temperature. After filtering off the slight turbidiy, the pH of the filtrate is adjusted to 6.5 – 6.8 by the addition of glacial acetic acid. The solution is then concentrated to half its volume and the resulting precipitate is filtered affording 3β-tridigitosyloxy-14,21-dihydroxy-5β, 14β-pregnan20-one $\nu_{max}^{CHCl_3}$ 3100 and 3625 (OH) and 1696 cm$^{-1}$ (CO).

In a similar manner periplocin, digoxin and gitoxin are respectively converted to 3β-cymarosyl-glucosyloxy-5,14,21-trihydroxy-5β,14β-pregnan-20-one, 3β-tridigitosyloxy-12β,14,21-trihydroxy-5β,14β-pregnan-20-one and 3β-tridigitosyloxy-14,16β,21-trihydroxy-5β,14β-pregnan-20-one when treated as described above.

EXAMPLE 3

22-Cyano-3β,14-dihydroxy-5β-card-20(22)-enolide 3-acetate

A solution of ethyl cyanoacetate (2.26 g) in methanol (10 ml) is added to an ice-cold methanolic solution of sodium methoxide, prepared by reacting sodium (0.46 g) and methanol (20 ml). After stirring for 5 minutes, a solution of 3β,14,21-trihydroxy-5β,14β-pregnan-20-one 3-acetate (4.16 g), obtained as described in Example 1, in methanol (15 ml) is added. The reaction is allowed to proceed at room temperature for 1 hour. Neutralization with 2N hydrochloric acid affords a precipitate, which is purified by crystallization from isopropanol to give the title compound, m.p. 247° – 252° $\nu_{max}$ (KBr pellet) 3500 (OH), 2230 (CN), (1760 (5-membered lactone), 1707 (acetate) and 1612 cm$^{-1}$ (double bond).

In a similar manner the 3-propionate and 3-butyrate of 3β,14,21-trihydroxy-5β,14β-pregnan-20-one, described in Example 1, are respectively converted to the 3-propionate and 3-butyrate of 22-cyano-3β,14-dihydroxy-5β-card-20(22)-enolide when treated as above with ethyl cyanoacetate and sodium methoxide.

Similarly 3β,14,21-trihydroxy-5β,14β-pregnan-20-one, 3β,5,14,21-tetrahydroxy-5β,14β-pregnan-20-one, 3β,12β,14,21-tetrahydroxy-5β,14β-pregnan-20-one and 3β,14,16β,21-tetrahydroxy-5β,14β-pregnan-20-one, obtained in Example 1, are converted to 22-cyano-3β,14-dihydroxy-5β-card-20(22)-enolide, 22-cyano-3β,5,14-trihydroxy-5β-card-20(22)-enolide, 22-cyano-3β,12β,14-trihydroxy-5β-card-20(22)-enolide and 22-cyano-3β,14,16β-trihydroxy-5β-card-20(22)-enolide, respectively, when treated as above.

Again similarly the 3-acetates, 3-propionates and 3-butyrates of 3β,5,14,21-tetrahydroxy-5β,14β-pregnan-20-one, 3β, 12β,14,21-tetrahydroxy-5β,14β-pregnan-20-one and 3β,14,16β,21-tetrahydroxy-5β,14β-pregnan-20-one, obtained in Example 1, are converted to the 3-acetates, 3-propionates and 3-butyrates of 22-cyano-3β,5,14-tri-hydroxy-5β-card-20(22)-enolide, 22-cyano-3β,12β,14-tri-hydroxy-5β-card-20(22)-enolide and 22-cyano-3β,14,16β-tri-hydroxy-5β-card-20(22)-enolide, respectively, when treated as above.

EXAMPLE 4

22-Cyano-14-hydroxy-3β-tridigitosyloxy-5β-card-20(22)-enolide

A solution of ethyl cyanoacetate (3.69 g) in methanol (15 ml) is added to an ice-cold methanolic solution of sodium methoxide, prepared from sodium (0.75 g) and methanol (38 ml). After stirring for 5 minutes at room temperature a solution of 3β-tridigitosyloxy-14,21-dihydroxy-5β,14β-pregnan-20-one (5 g), obtained as described in Example 2, in methanol (60 ml) is added. The mixture is allowed to react for 1 hour at room temperature, is acidified with 2N hydrochloric acid and is extracted with chloroform. The extracts are washed to neutrality, dried and evaporated. The residue is chromatographed on silica gel. Further purification by crystallization from acetone affords the title product, m.p. 245 – 248°, $\nu_{max}$ (KBr pellet) 3540 (OH), 2230(CN), 1766 and 1740 (5-membered ring lactone) and 1615 cm$^{-1}$ (double bond).

In a similar manner, 3β-cyamarosyl-glucosyloxy-5,14,21-trihydroxy-5β,14β-pregnan-20-one, 3β-tridigitosyloxy-12β,14,21-trihydroxy-5β,14β-pregnan-20-one and 3β-tridigitosyloxy-14,16β,21-trihydroxy-5β,14β-pregnan-20-one, obtained in Example 2, are respectively converted to 22-cyano-3β-cyamarosyl-glycosyloxy-5,14-dihydroxy-5β-card-20(22)-enolide, 22-cyano-12β,14-dihydroxy-3β-tridigitosyloxy-5β-card-20(22)-enolide and 22-cyano-14,16β-dihydroxy-3β-tridigitosyloxy-5β-card-20(22)-enolide when treated as above with ethyl cyanoacetate and sodium methoxide.

EXAMPLE 5

21,23-Epoxy-3β,14-dihydroxy-23-methoxy-24-nor-5β,14β-chola-20,22-diene-22-carbonitrile 3-acetate An ethereal solution of diazomethane is added rapidly to an ice-cold solution of 22-cyano-3β,14-dihydroxy-5β-card-20(22)-enolide 3-acetate (6.29), obtained as described in Example 3, in methylene chloride (190 ml), until the evolution of nitrogen has ceased. The reaction mixture is then stirred at room temperature for 21 hours and the solvents are removed by blowing nitrogen over the solution warmed to 60°. The residue is chromatographed on silica gel, eluted with 30% ethylacetate in benzene and crystallization of the eluted product with methylene chloride-diisopropyl ether affords the title product, m.p. 195° – 197° $\nu_{max}$ (KBr pellet): 3535 (OH), 2220 (CN), 1722 (CO of the acetate) and 1610, 1580 (furyl group). In a similar manner the 3-propionate and 3-butyrate of 22-cyano-3β,14-dihydroxy-5β-card-20(22)-enolide, obtained in Example 3, are converted to the 3-propionate and 3-butyrate of 21,23-epoxy-3β,14-dihydroxy-23-methoxy-24-nor-5β,14β-chola-20,22-diene-22-carbonitrile, respectively when treated as above with diazomethane.

Similarly 22-cyano-3β,14-dihydroxy-5β-card-20(22)-enolide, 22-cyano-3β,5,14-trihydroxy-5β-card-20(22)-enolide, 22-cyano-3β,12β,14-trihydroxy-5β-card-20(22)-enolide, 22-cyano-3β,14,16β-trihydroxy-5β-card-20(22)-enolide, obtained in Example 3 are converted to 21,23-epoxy-3β,14β-dihydroxy-23-methoxy-24-nor-5β,14β-chola-20,22-diene-22-carbonitrile, 21,23-epoxy-3β,5,14-trihydroxy-23-methoxy-24-nor-5β,14β-chola-20,22-diene-22-carbonitrile, 21,23-epoxy-3β,12β,14-trihydroxy-23-methoxy-24-nor-5β,14β-chola-20,22-diene-22-carbonitrile and 21,23-epoxy-3β,14,16β-trihydroxy-23-methoxy-24-nor-5β,14β-chola-20,22-diene-22-carbonitrile, respectively when treated as above with diazomethane.

Again similarly the 3-acetates, 3-propionates and 3-butyrates of 22-cyano-3β,5,14-trihydroxy-5β-card-20(22)-enolide; 22-cyano-3β,12β,14-trihydroxy-5β-card-20(22)-enolide and 22-cyano-3β,14,16β-trihydroxy-5β-card-20(22)-enolide, obtained in Example 3, are converted to the 3-acetates, 3-propionates and 3-butyrates of 21,23-epoxy-3β,5,14-trihydroxy-23-methoxy-24-nor-5β,14β-chola-20,22-diene-22-carbonitrile, 21,23-epoxy-3β,12β,14-trihydroxy-23-methoxy-24-nor-5β,14β-chola-20,22-diene-22-carbonitrile and 21,23-epoxy-3β,14,16β-trihydroxy-23-methoxy-24-nor-5β,14β-chola-20,22-diene-22-carbonitrile, respectively, when treated as above with diazomethane.

Again similarly 22-cyano-14-hydroxy-3β-tridigitosyloxy-5β-card-20(22)-enolide, 22-cyano-3β-cyamarosyl-glucosyloxy-5,14-dihydroxy-5β-card-20(22)-enolide, 22-cyano-12β,14-dihydroxy-3β-tridigitosyloxy-5β-card-20(22)-enolide and 22-cyano-14,16β-dihydroxy-3β-tridigitosyloxy-5β-card-20(22)-enolide, described in Example 4, are respectively converted to 21,23-epoxy-14-hydroxy-23-methoxy-3β-tridigitosyloxy-24-nor-5β,14β-chola-20,22-diene-22-carbonitrile, 3β-cyamarosyl-glucosyloxy-21,23-epoxy-5,14-dihydroxy-23-methoxy-24-nor-5β,14β-chola-20,22-diene-22-carbonitrile, 21,23-epoxy-12β,14-dihydroxy-23-methoxy-3β-tridigitosyloxy-24-nor-5β,14β-chola-20,22-diene-22-carbonitrile and 21,23-epoxy-14,16β-dihydroxy-23-methoxy-3β-tridigitosyloxy-24-nor-5β,14β-chola-20,22-diene-22-carbonitrile when treated as above with diazomethane.

We claim:
1. A compound of formula

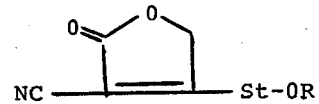

in which St—OR represents rings A, B, C and D of naturally-occuring 3β-oxygenated aglycones with their respective substituents attached thereto selected from the group consisting of digitoxigenin, periplogenin, digoxigenin and gitoxigenin, and R represents a glycosidic group naturally associated with the above aglycones and in which the cyanolactone ring is attached to the steroid moiety St at position 17β.

2. 21,23-Epoxy-14-hydroxy-23-methoxy-3β-tridigitosyloxy-24-nor-5β,14β-chola-20,22-diene-22-carbonitrile.

3. 22-Cyano-14-hydroxy-3β-tridigitosyloxy-5β-card-20(22)-enolide, as claimed in claim 1.

* * * * *